United States Patent [19]

Scholz

[11] Patent Number: 4,934,814
[45] Date of Patent: Jun. 19, 1990

[54] METHOD OF AND DEVICE FOR DETERMINING THE QUALITY OF RUNNING YARNS

[75] Inventor: Klaus-Dieter Scholz, Bobingen, Fed. Rep. of Germany

[73] Assignee: Hoechst Aktiengesellschaft, Fed. Rep. of Germany

[21] Appl. No.: 209,645

[22] Filed: Jun. 21, 1988

[30] Foreign Application Priority Data

Jun. 24, 1987 [DE] Fed. Rep. of Germany ....... 3720835

[51] Int. Cl.$^5$ ................................. G01N 21/89
[52] U.S. Cl. ..................... 356/238; 356/430
[58] Field of Search ........... 356/238, 430; 364/470, 364/552; 250/562, 572; 19/0.21, 0.22, 0.23

[56] References Cited

U.S. PATENT DOCUMENTS

| | | | |
|---|---|---|---|
| 3,543,360 | 12/1970 | Fertig | 356/430 X |
| 3,729,635 | 4/1973 | Shottenfeld et al. | 364/470 X |
| 3,758,216 | 9/1973 | Stutz | 356/430 |
| 3,986,037 | 10/1976 | Faulhaber | 250/562 |
| 4,051,722 | 10/1977 | Feller | 364/470 X |

FOREIGN PATENT DOCUMENTS 2749563 6/1979 Fed. Rep. of Germany.
2933297 3/1981 Fed. Rep. of Germany.

Primary Examiner—Davis L. Willis
Assistant Examiner—Matthew W. Koren
Attorney, Agent, or Firm—Connolly and Hutz

[57] ABSTRACT

Method of determining the quality characteristic of running yarns, in which the number of yarn imperfections is ascertained with the aid of fluff counters, wherein the thread passes through at least three fluff sensors of the same type arranged one after another, whose counting pulses, which are emitted upon passage, by a yarn section of the freely selectable length L, are converted into a length-related average R, highly deviant individual measurement results being regarded as outlier values and not being included in the averaging.

13 Claims, 2 Drawing Sheets

METHOD OF AND DEVICE FOR DETERMINING THE QUALITY OF RUNNING YARNS

DESCRIPTION

The present invention relates to a method of determining the quality characteristics of running yarns with the aid of fluff counters.

With regard to the production of yarns in the textile fiber industry or man-made fiber industry it is known to employ ray-optic devices, for example light barriers, to monitor running yarns or fluctuations in diameter and, especially, for protruding filaments, i.e. fluff or snarls.

A device of this type for monitoring a single running thread or yarn for fluctuations in diameter and for protruding filaments with the aid of a light barrier operating in the infrared region is known, for example, from the German Offenlegungsschrift No. 2,933,297.

In the production of warp beams, sheets of a few hundred unwinding yarns are monitored with similar light barriers. With this procedure, only relatively coarse yarn defects and broken yarn are identified as defects; these light barriers are not able to recognize individual broken filaments of individual yarns.

For the purposes of testing and quality control unwinding warp thread sheets have so far been monitored visually in a test beaming creel, and assessed in this way.

It is an obvious idea to monitor test beaming creels of such type with one light barrier each, or, otherwise, with one so-called fluff counter each, per running yarn. However, arrangements of such type do not yield reproducible quality characteristics for unwinding warp yarn sheets of a beaming creel. In fact, it has emerged that with the conventional measurement methods measurement results are recorded in statistical sequence, which lie far outside the values that correspond to the actual quality of the measured thread. The reasons for such outlier results are largely unknown. However, they lead to the fact that the assessment of the quality of a thread is not possible in practice using measurement methods of such type, so that it is necessary, as before, to assess the running thread visually.

There is already known from DE-A-2,749,563 a method for recognizing periodic thickness fluctuations in yarns, wherein the yarn passes through several light barriers lying one after another at specified separations in the thread path. In this known method, the light barrier separation is set so that the measured yarn thickness variation is in phase at all light barriers. If this is the case, the desired period length is equal to, or an integral multiple of the light barrier separation.

This expensive device is suitable only for recognizing periodically occurring thickness fluctuations, but not for determining and marking the quality of running yarns.

Surprisingly, it has now emerged that automatic fluff counting also makes it possible to obtain a numerical value which reflects the quality of the thread well and which can be reproduced well, if, according to the invention, the thread passes through at least three fluff sensors of the same type arranged one after another, whose counting pulses, which are emitted upon passage by a yarn section of the freely selectable length L, are converted into a length-related average R, highly deviant individual measurement results being regarded as outlier values and not being included in the averaging.

Since eliminating individual measurement results from a measurement series normally leads to an average of reduced reliability, it could not be expected here that this measure produces an easily reproducible measured value for the thread which marks its quality far better than an average calculated from a much higher number of individual measurements in the usual way.

In detail, the method according to the invention is conducted in such a way that the thread to be assessed is caused to pass in sequence through at least three fluff sensors of the same type ($S_1$, $S_2$, $S_3$ ... $S_n$). The counting pulses emitted by the individual sensors during the passage by a thread section of the freely selectable length L, which is not too short, are added separately to the pulse totals $X_1$ to $X_n$ for each of the fluff sensors $S_1$ to $S_n$, and are stored. The indices i (1 to n) enable the allocation of the pulse totals X to the individual sensors, in that the pulse total is provided with the same index as the corresponding sensor. This means that the indices i pass through the values of the integers from 1 to n.

If, in the population of values $X_1$ to $X_n$ obtained, there are one or more values $X_j^*$ deviating very markedly from the remaining values $X_i$—so-called outlier values—they are not taken into account during averaging.

Given N outlier values, the following holds for the average:

$$\overline{X}^* = \frac{\sum\limits_{i=1}^{i=n} X_i - \sum\limits_{j=1}^{j=N} X_j^*}{n - N} \quad (I)$$

This corrected average $\overline{X}$HD corr can also be determined by not including the outlier values in the averaging in the first place.

Independently of the computing strategy, we obtain the value of $\overline{X}$HD corr defined by formula I.

After scaling to a length unit of the measured thread length L, $\overline{X}$HD corr yields the length-related average R as quality parameter $$R = \frac{\overline{X}_{corr}}{L} \quad (II)$$

which represents an objective yardstick for assessing the thread quality.

If no outlier value $X_j^*$ is present in a population of values $X_1 \ldots X_n$, then $\overline{X}$ is computed from all these values, and thereafter the value of R is computed from $$R = \frac{\overline{X}}{L} \quad (IIa)$$

Of course, $\overline{X}$ can also be derived from formula I with N=zero.

$\overline{X}$ or $\overline{X}$HD corr can also be used as quality parameters, if, for example, the same thread length L is continually measured during an operating cycle. In this case, it is possible to omit the scaling to the length unit, that is to say the division of $\overline{X}$ or $\overline{X}$HD corr by L.

The term "outlier value" can be defined differently depending on the formulation of the problem, the matters of interest and the measuring device.

An outlier value can be identified by the fact that its individual square deviation from the average of all square deviations is more than $\kappa$ times as large as the average of all individual square deviations.

$$(\Delta X_j^*)^2 \geq \kappa \cdot \frac{\sum\limits_{i=1}^{i=n} (\Delta X_i)^2}{n} \quad \text{(III)}$$

where $\Delta X_i = X_i - \overline{X}$ it is expedient with regard to 3 fluff sensors connected one after another for $\kappa$ to lie within the range from 1.78 to 1.85, preferably 1.8 to 1.83 and $$\overline{X} = \frac{\sum\limits_{i=1}^{i=n} X_i}{n}$$

A deviant individual value will be the more readily indexed as an outlier value, the smaller $\kappa$ is selected.

For example, it is possible to regard as outlier value a value $X_j^*$ whose individual square deviation from the average $\overline{X}$ of all measured values $X_i$ is more than $\lambda$ times as large as the average from the individual square deviations of all measured values $X_i$ with the exception of $X_j^*$:

$$(\Delta X_j^*)^2 \geq \lambda \cdot \frac{\sum\limits_{i=1}^{i=n} (\Delta X_i)^2 - (\Delta X_j^*)^2}{n-1} \quad \text{(IV)}$$

$\Delta X_i$ or $\Delta X_j^*$ having the meaning given above and $\lambda$ being selected in the range from 2.7 to 3.5, preferably from 3 to 3.2.

If, now, only a single outlier value is expected, which is always the case, for example, concerning the application of three sensors, then the following procedure has proved itself. Firstly, for each possible pairing without repetition of the pulse totals $X_i$, namely $X_1/X_2$, $X_1/X_3$ . . . , $X_1/X_n$; $X_2/X^3$ . . . $X_2/X_n$, the values of the differences $D_{i1, i2}$ $$|X_{i1} - X_{i2}| = D_{i1,i2} \quad \text{(VII)}$$

are computed. As may be seen from the equation VII, the indices i1 and i2 indicate that the value of D concerned has come from the values of the pulse total $X_{i1}$ and $X_{i2}$.

Correspondingly, the indices of the magnitudes Y and Q named further below indicate from which pairing of X values they have come.

Accordingly, for n fluff sensors located one after another, we have $$M = \sum_{r=1}^{r=n-1} r \quad (r = 1, 2 \ldots n-1)$$

values for $D_{i1, i2}$; accordingly, for 3 sensors there are 3, or for 4 sensors 6 and for 5 sensors 10 difference amounts $D_{i1, i2}$.

Thereafter, the numerical value of about 1, preferably 1 itself, is further added
(a) either to all values $D_{i1, i2}$ or
(b) only to such values $D_{i1, i2}$ as vanish,
and the minimum value $Y^m_{i1, i2}$ is extracted from the new group of values $Y_{i1, i2}$ so obtained. Next, the quotients $$Q_{i1,i2} = \frac{Y_{i1,i2}}{Y^m_{i1,i2}}$$

are formed and compared with a limiting value G, which is suitable for defining outlier results and lies in the range from 2 to 4, preferably at 3.

If none of the $Q_{i1, i2}$ values obtained exceeds this limiting value, then the $X_i$ population contains no outlier, and all the $X_i$ values are used as described above to determine the average X, and the quality parameter R is determined therefrom, if desired.

Depending on the subprogram stored in the computer, it can be advantageous to compute not all possible $Q_{i1, i2}$ values, but, initially, to determine both the minimum value $Y_{i1, i2}^m$ and also the maximum value $Y_{i1, i2}^{max}$ and the quotient $$Q_{max} = \frac{Y^{max}_{i1,i2}}{Y^m_{i1,i2}}$$

In this way, only the largest of the possible quotients $Q_{i1, i2}$ is obtained. If it is equal to or smaller than G, the $X_i$ population contains no outlier.

The demonstrated outlier value of $X_1$ is identified and eliminated, and the average $\overline{X}HU^*$ is computed from the remainder of the values $X_i$, as described above, and used to compute R.

To identify the outlier value $X_j^*$, the indices of the excessive $Q_{i1, i2}$ values are brought in. In a population of 3 $x_i$ values, 2 excessive $Q^*_{i1, i2}$ values are obtained, and with reference to 5 $X_i$ values, for example, 4. In this connection, the outlier value is the pulse total value $X_i$ whose index i recurs in all excessive $Q^*_{i1, i2}$ values.

If the presence of an outlier value has resulted from a comparison of $Q_{max}$ and G, the indexing of the minimum Y value ($Y_{i1, i2}^m$) is brought in to identify the outlier value $X_j^*$: the outlier value is the value whose index does not occur in $Y_{i1, i2}^m$:

$$j \neq i1, j \neq i2.$$

It is expedient to insert 3 to 5, preferably 3, fluff sensors one after another in the path of the thread to be assessed.

The point is that, surprisingly enough, the use of as few as three sensors per thread path yields easily reproducible, informative measurements, so that it is mostly possible to do away with the expense of several sensors. This simple method with only three sensors is all the more surprising since, in the case of an outlier, only the results from two sensors are taken into account there.

In connection with the preferred employment of only three sensors, a further simple practical method consists in forming the three differences of the three measured values $X_i$ in a way similar to that already described, generating finite values by adding preferably the number 1 to zero values, and then forming the three quotients Q. If, now, the largest value of these three quotients lies below the present limit G, all three values $X_i$ are averaged to give the value $\overline{X}$ in the other case only the two values $X_{i1}$ and $X_{i2}$ are used, which form the smallest value for the difference $D_{i1, i2} = |X_{i1} - X_{i2}|$. This practical method is distinguished by a particularly high test speed. It therefore has particular importance for the installation of a real time system.

Very good results are obtained if light barriers are employed as fluff sensors. In principle, these can all be installed in the same position relative to the direction of thread path. However, it is advantageous if the sensors are arranged one after another but are twisted at a constant angle in the plane perpendicular to the direction of thread path.

A particularly good stabilization of the thread path and few outlier values are obtained if the fluff sensors are arranged on an arc, preferably a circular arc, to which the threads are forcibly led.

A particular embodiment of the method according to the invention consists in employing as fluff sensors light barriers with classification electronics connected downstream, which also sort the fluff numbers by fluff size, it also being possible to distinguish between fluff in the transverse and longitudinal directions, and in evaluating by class the classified pulses of the fluff sensors so obtained.

Further additional information about the thread quality can be obtained using the method, if the acquisition of events takes place sectionally, i.e. in sectional lengths of thread related to the selected test length, so that error accumulations or periodically occurring errors can be recognized and assigned to specific causes.

A device for executing the method according to the invention comprises at least three fluff sensors located one after another in the thread path, if necessary a device for measuring the length L of the thread passing through, insofar as this is not provided already dimensioned, and an arithmetic unit which, in addition to the pulse total values $X_i$, sums the counting pulses for each sensor and stores these pulse total values, tests the sums obtained, in accordance with the criteria specific to the method as given above, for outlier values and eliminates such values, and then forms the average of all pulse total values $X_i$ to be considered, and, if desired, further scales this average to a thread length unit.

Any set-up known for the purpose can be used as device for measuring the thread length, for example a measuring roller of specified circumference, which is rotated in a non-slip fashion by the running thread, and whose number of revolutions is recorded.

Such a device according to the invention can be further supplemented both before and after the group of fluff sensors by a feed system which is located in the thread path and may be controlled independently and in a stepless fashion, the two feed systems being controlled in such a way that for various yarn types the correct test tension is set and maintained. The acceleration of the thread sheet up to the test speed or the final breaking after the completed test is preferably done via an electronic control in such a way that no threading-in is required.

The arithmetic unit of the device according to the invention tests the stored pulse total values $X_i$ for outlier values, in that, firstly, by averaging all the pulse totals relating to the selected thread length L, the auxiliary computational quantity X is formed, and then a computer program is run, which checks whether the individual $X_i$ values satisfy one of the formulae III or IV given above. Of course, this testing is alternative, i.e. the test needs to be carried out on only one of the formulae mentioned, according to choice. An $X_i$ value satisfying one of the formulae is an outlier value, and is erased from the memory by the computer.

An alternative computer program for identifying outlier values firstly determines, for each possible pairing of the pulse totals $X_i$, the difference amounts, then adds
(a) either to all difference amounts obtained or
(b) only to the difference amounts which vanish a numerical value of about 1, preferably 1 itself, and stores the intermediate values $Y_{i1,i2}$ obtained, the indices also being stored as identification characteristics.

The computer now searches out from the group of Y values obtained the minimum value $Y^m_{i1,i2}$, and forms for all remaining Y values the quotient $$Q_{i1,i2} = \frac{Y_{i1,i2}}{Y^m_{i1,i2}}$$

The next program step consists in a comparison of the Q values with a stored limiting value G, a selection of all $Q^*$ values, which exceed this limiting value, and in the determination of the index which occurs in all selected $Q^*$ values. The index so obtained is the index of the pulse total $X_i$ which is to be regarded as outlier value.

Accordingly, from among the group of the stored $X_i$ values, the computer program identifies and treats as outlier value the one which exhibits the index present in all selected Q values.

An alternative evaluation of the $Y_{i1,i2}$ values obtained consists in having the computer search out not only the minimum value $Y_{i1,i2}{}^m$, but also the maximum value $Y_{i1,i2}{}^{max}$ and the quotient $$Q_{max} = \frac{Y^{max}_{i1,i2}}{Y^m_{i1,i2}}$$

If $Q_{max}$ is smaller than G, then the population $X_i$ contains no outlier, if $Q_{max}$ is larger than G then it does contain an outlier. The latter has the index that does not occur in $Y_{i1,i2}{}^m$.

The computational treatment of the outlier values is aimed at eliminating these values from the averaging in a suitable fashion. This takes place by averaging according to the formula $$\overline{X}^* = \frac{\sum\limits_{i=1}^{i=n} X_i - X_1^*}{n - 1} .$$

In this connection, the arithmetic unit can operate, for example, in such a way that firstly $$\overline{X}^* = \frac{\sum\limits_{i=1}^{i=n} X_1}{n} ,$$

is formed and subsequently $$\overline{X}^* = \frac{n \cdot \overline{X} - X_i}{n - 1}$$

is computed, or that the outlier value $X_i^*$ is not even included in the averaging, but is eliminated from the memory of the $X_i$ value. Subsequently, the computer computes the average $\overline{XHU}^*$ from the remainder of the $X_i$ values, and, if desired, divides it by the length L of the measured thread section.

Independently of the computing strategy, the value of $\overline{XHU}^*$ is obtained from formula (I).

A set-up particularly suited for executing the method according to the invention is one in which each yarn of a warp thread sheet passes through two feed systems, and between them, at a defined yarn tension, at least three light barriers located one after another.

The fluff count per length unit as determined according to the invention, possibly coded in terms of predetermined size classes, may be used to determine quality characteristics which objectify the vague term "yarn quality" with reference to application.

By selecting the data processing program, it is possible, at a measuring device, to match these quality characteristics to the particular yarn (man-made yarn or multifilament yarn), the linear density (individual and overall linear density), the type of yarn (smooth, textured or high-twist) and the area of application.

The advantage of the method according to the invention lies not only in the simple matching to the task set, i.e. to the type of yarns employed and the quality requirements, but in addition the method according to the invention replaces a demanding, subjectively influenced, visual monitoring at the beaming creel with an objective, largely automated measurement method, which quickly reduces highly differentiated information.

These objective items of quality information can take the form of a test list or of a simple yes/no statement on quality, or they can, as required, even be used online to control preceding or subsequent production processes.

Figure 1A:
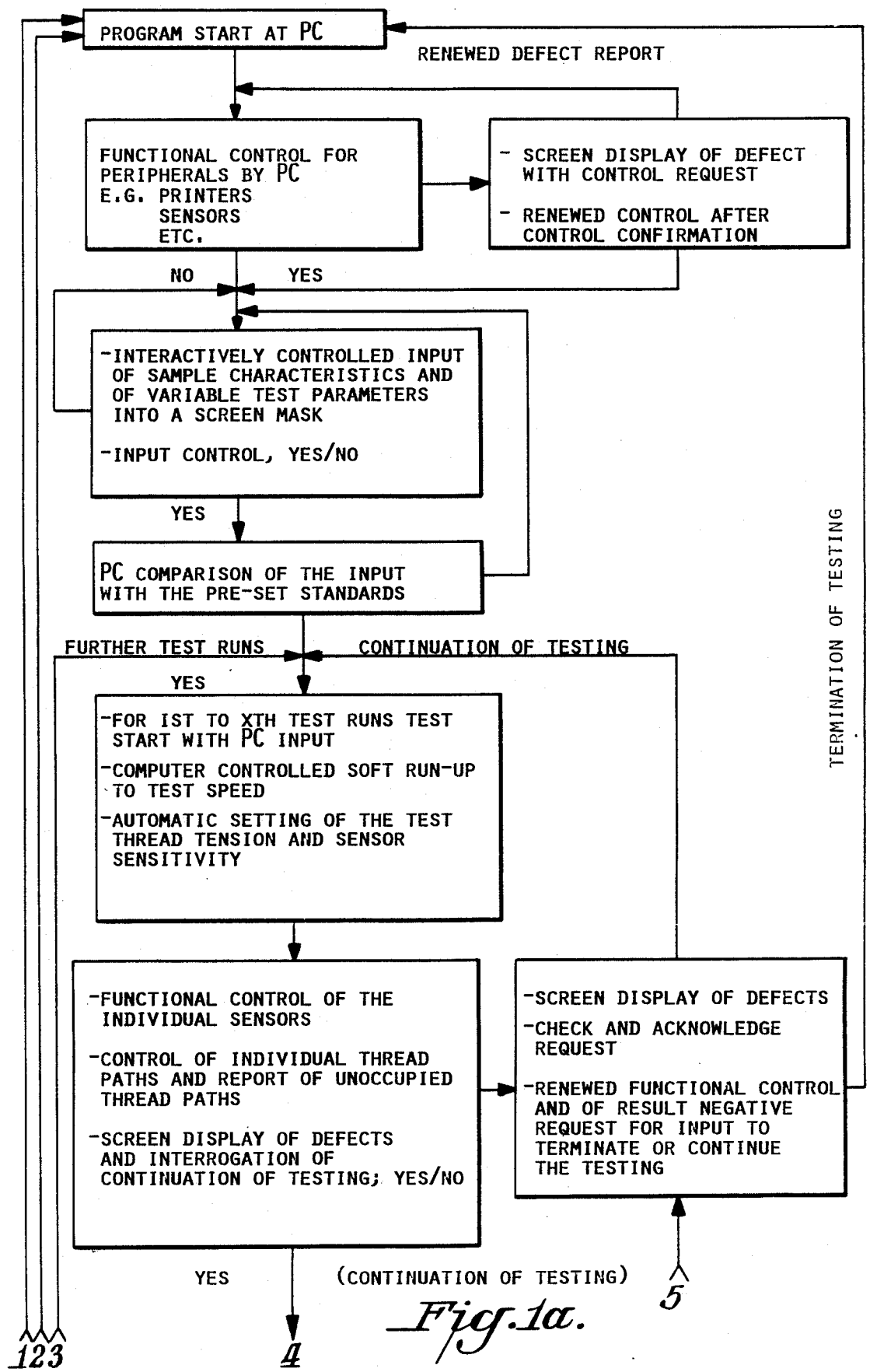
FIGS. 1a and 1b are flow diagrams illustrating the method of the present invention for determining the quality characteristics of running yarns.

The following illustrative embodiments exemplify the method according to the invention.

EXAMPLE 1

The test device according to the invention comprised three light barriers located one after another, which were accommodated on a circular arc with a radius of curvature of 0.5 m. The beam direction of the light barriers lay in a plane standing vertically on the thread path. The entire light barrier set-up lay between two separately controllable feed systems, which maintained a constant thread tension of 5 cN during the test run.

An arithmetic unit was inserted downstream of the light barriers and it recorded, summed up and stored the light barrier pulses. In a further step, the pulse totals of the individual counters were further processed in accordance with one of the methods described above.

The thread speed was set at 10 m/sec., and the thread path was started. After a run-up time of 15 seconds, within which a smooth and constant thread path was established, measurement was started and a thread length of 3000 m was measured off.

In this way, the following pulse totals were obtained from the three light barriers:

$$S_1: X_1 = 14; S_2: X_2 = 3; S_3: X_3 = 3.$$

Further treatment of these values in the computer produced the following intermediate results:

$$D_{1,2} = |X_1 - X_2| = 11$$

$$D_{1,3} = |X_1 - X_3| = 11$$

$$D_{2,3} = |X_2 - X_3| = 0$$

1 was added to the value $D_{2,3}$, whose amount vanishes, thus obtaining $Y_{1,2} = 11$, $Y_{1,3} = 11$, $Y_{2,3} = 1$.

Selection of the smallest Y value, and division of the remaining Y values by the smallest yielded:

$$Q^*_{1,2} = \frac{Y_{1,2}}{Y_{2,3}} = \frac{11}{1} = 11,$$

and analogously $Q^*_{1,3} = 11$ and $Q_{2,3} = 1$. The limiting value G input into the computer was 3, and consequently $Q^*_{1,2}$ and $Q^*_{1,3}$ were assessed as being greatly excessive with a value of 11 each.

The index common to the two excessive $Q^*$ values was recognized by the computer as 1, so that $X_1$ was identified and eliminated as outlier value.

The average $\overline{X}HU^*$ finally formed from $X_2$ and $X_3$, was determined as 3 and output.

The same result was obtained using an alternative computer program:

Selection of the largest and smallest Y values, and division of the largest Y value by the smallest yielded:

$$Q^*_{max} = \frac{Y_{1,2}}{Y_{2,3}} = \frac{11}{1} = 11.$$

Since the limiting value G input into the computer for the $Q_{max}$ from $Y_{max}$ and $Y_{min}$ had the value 3, by comparison with the result $Q_{max} = 11$, the computer recognized the presence of an outlier value.

As this outlier value, it identified the sensor $S_1$ with $X_1 = 14$ which did not participate in the smallest Y difference.

Upon 10 repetitions of the measurement of the same yarn quality, all measurement results $\overline{X}$ lay between 2 and 5. This means that the method is very easily reproducible. In connection with the measurement of an identical yarn quality using the conventional method with a light barrier, $\overline{X}$ values of between 2 and 10 were obtained 6 times, and $\overline{X}$ values of between 10 and 20 were obtained 4 times, there being 10 measurements. Consequently, the known method is not suitable for perfect assessment of the yarn quality.

For production testing a testing device is being set up with 20 neighboring thread run positions with 3 light barriers located one after another.

EXAMPLE 2

A measuring device as described in Example 1, however with 4 light barriers, was employed to measure a yarn. During a measuring run, which indicated an outlier result, the following data were determined and processed to the $\overline{X}$ value via the intermediate values given:

$$X_1 = 4; X_2 = 5; X_3 = 13; X_4 = 3$$

$$D_{1,2} = 1; D_{1,3} = 9; D_{1,4} = 1; D_{2,3} = 8; D_{2,4} = 2; D_{3,4} = 10$$

$$Y_{1,2} = 1; Y_{1,3} = 9; Y_{1,4} = 1; Y_{2,3} = 8; Y_{2,4} = 2; Y_{3,4} = 10$$

from the smallest Y values the computer used the one with the smallest index number:

$$Y_{1,2}$$

$$Q_{1,2} = 1; Q_{1,3} = 9; Q_{1,4} = 1; Q_{2,3} = 8; Q_{2,4} = 2;$$

$$Q_{3,4} = 10$$

Q values > 2 are $Q^*_{1,3}$; $Q^*_{2,3}$; $Q^*_{3,4}$ (outlier values)

Common index: 3;
Outlier value of the pulse sum = $X_3$.
Consequently, averaging from $X_1$, $X_2$ and $X_4$.
Result $\overline{X}32$ 4.

Upon 10 repetitions of the measurement of the identical yarn quality, results of between 3 and 5 were obtained on 6 occasions, and result 6 was obtained on one occasion. Consequently, the reproducibility of the measurement is completely satisfactory for the automatic monitoring of the beaming creels. By contrast, for 10 measurements a single counter indicated fluff counts over 30 on three occasions.

EXAMPLE 3

A measuring device according to Example 1, but in which inserted after the three fluff sensors was an assessment circuit for large, average and small fluffs, and also for fluff clusters, was employed to measure a yarn.

The following individual results were indicated by the sensors:

| Fluff size | $X_1$ | $X_2$ | $X_3$ |
|---|---|---|---|
| Large | 1 | 0 | 0 |
| Average | 3 | 1 | 0 |
| Small | 11 | 2 | 3 |
| Cluster | 0 | 0 | 0 |

For a limiting value G of 3 input into the computer, the evaluation by classes of the $X_i$ values carried out by the computer in accordance with the methods given in Examples 1 and 2 yielded:

Large fluffs $D_{1,2}=1$ $Y_{1,2}=1$ $Q_{1,2}=1$ $D_{1,3}=1$ $Y_{1,3}=1$ $Q_{1,3}=1$ $D_{2,3}=0$ $Y_{2,3}=1$ $Q_{2,3}=1$ Average fluffs $D_{1,2}=2$ $Y_{1,2}=2$ $Q_{1,2}=2$ $D_{1,3}=3$ $Y_{1,3}=3$ $Q_{1,3}=3$ $D_{2,3}=1$ $Y_{2,3}=1$ $Q_{2,3}=1$ Small fluffs $D_{1,2}=9$ $Y_{1,2}=9$ $Q^*_{1,2}=9$ $D_{1,3}=8$ $Y_{1,3}=8$ $Q^*_{1,3}=8$ $D_{2,3}=1$ $Y_{2,3}=1$ $Q_{2,3}=1$ Accordingly, the following results are obtained
X for large fluffs: 0.3
X for average fluffs: 1.3
X for small fluffs: 2.5

With regard to all the measurements given in the examples, the measurement results were available immediately after the yarn had passed through the measuring length.

EXAMPLE 4

Figure 1B:
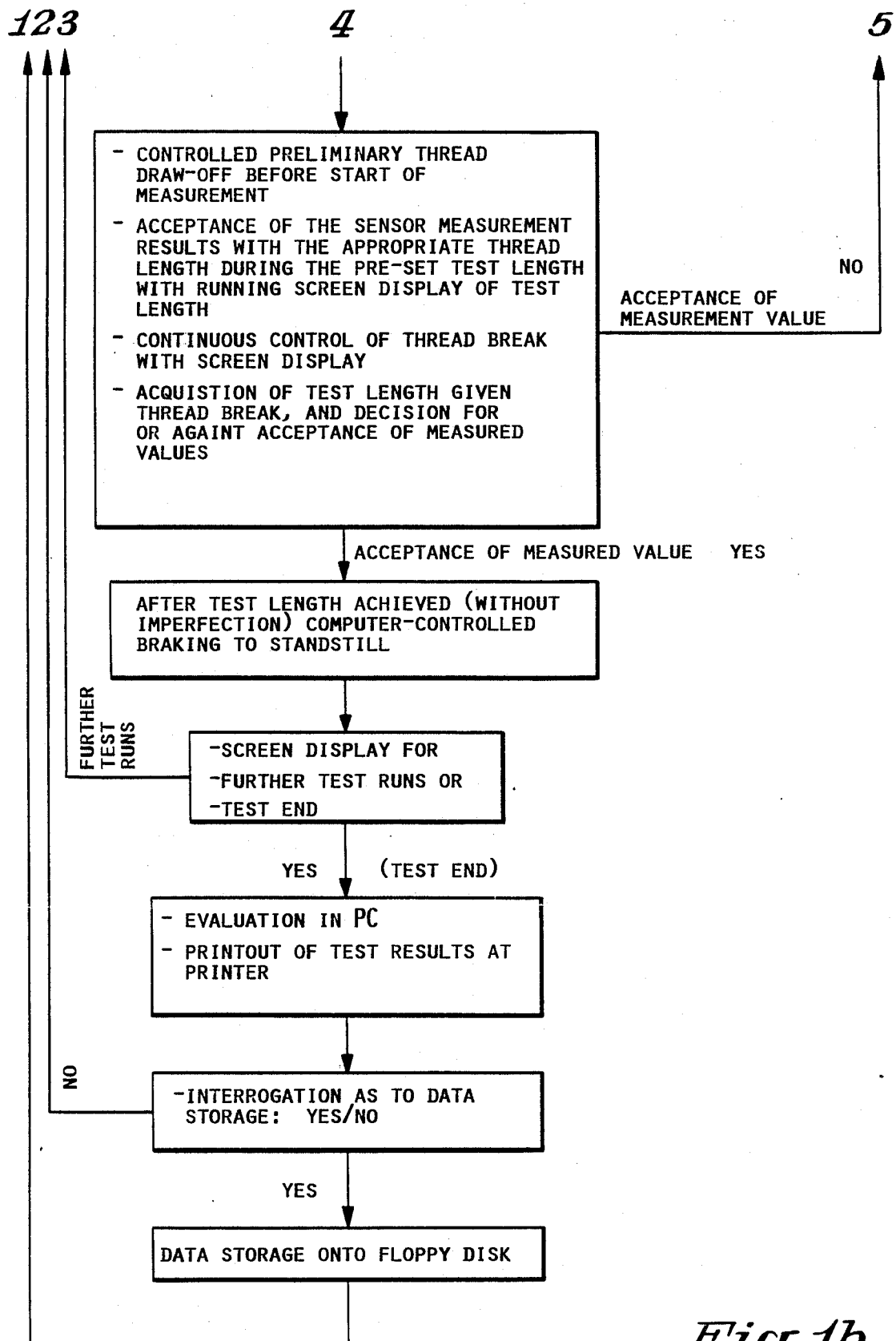

The flow chart reproduced in FIGS. 1a and 1b exemplifies a possible, practical embodiment of the method according to the invention and the measuring device employed therewith.

I claim:

1. Method of determining the quality characteristics of running yarns, in which the number of yarn imperfections is ascertained with the aid of fluff counters, comprising the steps of passing a thread through at least three fluff sensors of the same type arranged one after another, each sensor emitting counting pulses upon passage of a yarn section of a freely selectable length L, converting the counting pulses into a length-related average R, and excluding highly deviant individual measurement results from the averaging.

2. Method according to claim 1, wherein three to n fluff sensors $S_1$ to $S_n$ are arranged one after another in the direction of the thread path, adding separately the counting pulses emitted by the individual sensors during the passage by a thread section of the freely selectable length L, to the pulse totals $X_1$ to $X_n$ for each of the fluff sensors $S_1$ to $S_n$, storing the added pulses, and identifying and eliminating any values present of $X_j^*$ which deviate markedly from the remaining values of $X_i$ as outlier values, by calculating the average $\overline{x}HU^*$ with the formula $$\overline{X}^* = \frac{\sum_{i=1}^{i=n} X_i - \sum_{j=1}^{j=N} X^*_j}{n - N}$$

wherein N is the number of outlier values, and optionally using this value to compute the length-related average R as quality parameter $$R = \frac{\overline{X}^*}{L}$$

by scaling to a length unit of the measured thread length L.

3. Method according to claim 1 wherein the outlier value $X_i^*$ is identified in that it exhibits an individual deviation $\Delta X_i^*$ from the average of the individual deviations, which alternatively satisfies one of the following formulae:

$$(\Delta X^*_i)^2 \geq \kappa \cdot \frac{\sum_{i=1}^{i=n} (\Delta X_i)^2}{n}$$

or $$(\Delta X^*_i)^2 \geq \lambda \cdot \frac{\sum_{i=1}^{i=n} (\Delta X_i)^2 - (\Delta X^*_i)^2}{n - 1},$$

where $$\Delta X_i = \overline{X}_i - X$$

$$X = \frac{\sum_{i=1}^{i=n} X_i}{n}$$

κ denotes a number from 1.78 to 1.85 and
λ denotes a number from 2.7 to 3.5.

4. Method according to claim 1 wherein the identification of the outlier values takes place in the manner that, firstly, the values of the differences $D_{i1,i2}$ between the pulses of pulse pairings $$|X_{i1} - X_{i2}| = D_{i1,i2},$$

are computed for each possible pairing without repetition of the pulse totals $X_i$, thereafter, the numerical value of about 1, preferably 1 itself, is further added (a) either to all the values $D_{i1, i2}$ or (b) only to such values $D_{i1, i2}$ as vanish, and the minimum value $Y^m_{i1, i2}$ is extracted from the new group of values $Y_{i1, i2}$ so obtained, the quotients $$Q_{i1,i2} = \frac{Y_{i1,i2}}{Y^m_{i1,i2}}$$

are then formed, all the values of $Q^*_{i1, i2}$ exceeding a limiting value G are determined and, finally, from the population of $X_i$ values there is chosen as outlier value the one whose index j occurs in all values of $Q^*_{i1, i2}$.

5. Method according to claim 1 wherein three fluff sensors are employed, and the identification of the outlier values takes place in a manner that, firstly, the amounts of the differences $D_{i1, i2}$ between the pulses of pulse pairings $$|X_{i1} - X_{i2}| = D_{i1,i2},$$

are computed for each possible pairing without repetition of the pulse total $X_i$, thereafter, the numerical value of about 1, preferably 1 itself, is further added (a) either to all values $D_{i1, i2}$ or (b) only to such values $D_{i1, i2}$ as vanish, and the minimum value $Y^m_{i1, i2}$ and the maximum value $Y^{max}_{i1, i2}$ are extracted from the new group of values $Y_{i1, i2}$ so obtained, the quotient $$Q_{max} = \frac{Y^{max}_{i1,i2}}{Y^m_{i1,i2}}$$

is then computed, this value is compared with a limiting value G and, if $Q_{max} > G$, from the population of $X_i$ values there is chosen as outlier value the one whose index j is not contained in the index of $Y_{i1, i2}^m$.

6. Method according to claim 5, wherein the largest of the three quotients $Q_{i1, i2}$ is compared with G and, if it is smaller than G all three $X_i$ values are averaged for the value X, and, if it is larger than G, then in order to compute $\overline{X}$ only the two $X_i$ values are used which generate the smallest difference amount $$D_{i1,i2} = |X_{i1} - X_{i2}|$$

7. Method according to claim 1, wherein a light barrier is employed as fluff sensor.

8. Method according to claim 1, wherein a light barrier with classification electronics connected downstream is employed as fluff sensor.

9. Method according to claim 8, wherein the classified pulses of the fluff sensors are evaluated by classes.

10. Method according to claim 1, wherein 3 to 5 fluff sensors are located one after another in the thread path.

11. Device for determining objective quality parameters of a thread or yarn, comprising at least three fluff sensors located one after another in the thread path, optionally a device for measuring the length L of the thread passing through and an arithmetic unit which, in addition to the pulse total values $X_i$, sums the counting pulses for each sensor and stores these values, tests the group of the $X_i$ values obtained for outlier values $X_i^*$ and eliminates the latter, by determining an average $\overline{X}HU^*$ according to the formula $$\overline{X}^* = \frac{\sum_{i=1}^{i=n} X_i - \sum_{j=1}^{j=N} X_j^*}{n - N},$$

and scales the latter, optionally, to the thread length unit.

12. Device according to claim 11, supplemented both before and after the group of fluff sensors by a feed system which is located in the thread path and may be controlled independently and in a stepless fashion, the two feed systems being controlled in such a way that for various yarn types the correct test tension is set and maintained.

13. Device according to claim 11, supplemented both before and after the group of fluff sensors by a feed system which is located in the thread path and may be controlled independently and in a stepless fashion, wherein the acceleration of the feed systems up to the test speed or the braking after the completed test is preferably done via an electronic control in such a way that no threading-in is required.

* * * * *

UNITED STATES PATENT AND TRADEMARK OFFICE
CERTIFICATE OF CORRECTION

PATENT NO. : 4,934,814

DATED : June 19, 1990

INVENTOR(S) : Klaus-Dieter Scholz

It is certified that error appears in the above-identified patent and that said Letters Patent is hereby corrected as shown below:

Column 2, line 32, "$\overline{X}$HD corr" should be -- $\overline{X}_{corr}$ --;

line 36, "$\overline{X}$HD corr" should be -- $\overline{X}_{corr}$ --;

line 38, "$\overline{X}$HD corr" should be -- $\overline{X}_{corr}$ --;

line 57, "$\overline{X}$HD corr" should be -- $\overline{X}_{corr}$ --;

line 61, "$\overline{X}$HD corr" should be -- $\overline{X}_{corr}$ --;

Column 4, line 12, "$Y_{i1, i2}^{m}$" should be -- $Y_{i1, i2}^{m}$ --;

line 13, "$Y_{i1, i2}^{max}$" should be -- $Y_{i1, i2}^{max}$ --;

line 23, "$\overline{X}$HU*" should be -- $\overline{X}$* --;

line 34, "($Y_{i1, i2}^{m}$" should be -- ($Y_{i1, i2}^{m}$) --;

line 36, "$Y_{i1, i2}^{m}$" should be -- $Y_{i1, i2}^{m}$ --;

Column 6, line 24, "$Y_{i1, i2}^{m}$" should be -- $Y_{i1, i2}^{m}$ --;

line 25, "$Y_{i1, i2}^{max}$" should be -- $Y_{i1, i2}^{max}$ --;

line 35, "$Y_{i1, i2}^{m}$" should be -- $Y_{i1, i2}^{m}$ --;

line 43, "$X_1$*" should be -- $X_i$* --;

line 49, "$X_1$ " should be -- $X_i$ --;

line 55, "$\overline{x}$*" should be -- $\overline{X}$* --;

line 50, "$\overline{X}$*" should be -- $\overline{X}$ --;

line 61, "$\overline{X}$HU*" should be -- $\overline{X}$* --;

line 65, "$\overline{X}$HU*" should be -- $\overline{X}$* --;

Column 8, line 14, "$\overline{X}$HU*" should be -- $\overline{X}$* --;

Column 9, line 4, "$\overline{X}$32 4" should be -- $\overline{X}$ = 4 --;

UNITED STATES PATENT AND TRADEMARK OFFICE
CERTIFICATE OF CORRECTION

PATENT NO. : 4,934,814

DATED : June 19, 1990

INVENTOR(S) : Klaus-Dieter Scholz

It is certified that error appears in the above-identified patent and that said Letters Patent is hereby corrected as shown below:

In the claims:

Claim 2, line 10 (column 10, line 21), "$\bar{x}HU*$" should be -- $\bar{X}*$ --.

Claim 3, fourth formula (column 10, line 59), "X" should be -- $\bar{X}$ --;

Claim 5, last line, (column 11, lines 42), "$Y_{i1, i2}{}^m$" should be -- $Y^m_{i1, i2}$ --;

Claim 11, line 10, (column 12, line 23), "$\bar{X}HU*$" should be -- $\bar{X}*$ --.

Signed and Sealed this

Seventeenth Day of September, 1991

Attest:

HARRY F. MANBECK, JR.

*Attesting Officer*  *Commissioner of Patents and Trademarks*